United States Patent
Lauter

(10) Patent No.: US 6,575,892 B1
(45) Date of Patent: Jun. 10, 2003

(54) WATER TUB FOR APPLYING MAGNETIC FLUX TO HUMAN BODY

(75) Inventor: Robert Lauter, Auburn, IN (US)

(73) Assignee: Master Spas, Inc., Fort Wayne, IN (US)

( * ) Notice: Subject to any disclaimer, the term of this patent is extended or adjusted under 35 U.S.C. 154(b) by 0 days.

(21) Appl. No.: 09/588,145

(22) Filed: Jun. 2, 2000

(51) Int. Cl.$^7$ .............................. A61B 17/52; A61N 2/00
(52) U.S. Cl. ........................................................... 600/9
(58) Field of Search ................................ 600/9, 10, 11, 600/12, 13, 14, 15; 4/534, 538, 558; 607/85, 86, 87; 601/15

(56) References Cited

U.S. PATENT DOCUMENTS

| | | | |
|---|---|---|---|
| 2,212,326 A | * 8/1940 | Piken | 4/558 |
| 4,166,294 A | * 9/1979 | McGowan | 4/534 |
| 4,233,694 A | 11/1980 | Janosko et al. | |
| 5,366,435 A | 11/1994 | Jacobson | |
| 5,368,544 A | 11/1994 | Tran et al. | |
| 5,693,004 A | 12/1997 | Carlson et al. | |
| 5,738,624 A | 4/1998 | Zablotsky | |
| 5,842,966 A | 12/1998 | Markoll | |
| 6,004,257 A | * 12/1999 | Jacobson | 600/9 |

FOREIGN PATENT DOCUMENTS

JP    411342057 A   * 12/1999

OTHER PUBLICATIONS

Technology Update—Article/advertizement literature: "How do professional athletes help fight pain without chemical or surgery". (1) sheet, No date given.

Herrington—Article/advertizement literature: "For Men and Women! At Last, Bring BioMagnetic To Tired, Sore Feet With Florsheim MagnetForce™ Golf Shoes!". (1) sheet, No date given.

* cited by examiner

Primary Examiner—Max F. Hindenburg
Assistant Examiner—Brian Szmal
(74) Attorney, Agent, or Firm—George Pappas

(57) ABSTRACT

A water tub for applying magnetic flux to a human back and neck including a water retaining wall whereagainst a human may place his back. Permanent magnets are affixed on the outside surface of the water retaining wall with an adhesive. The retaining wall and adhesive are made of non-magnetic materials. The magnetic flux field of each of the magnets travels through the retaining wall and beyond the wall inside surface and into a human's back placed adjacent thereto. A neck support pillow made of compressible foam is supported generally at the top of the water retaining wall and is adapted to support a human's neck. Magnets are embedded within the foam whereby the magnetic flux field thereof travels out from the pillow and beyond the inner surface into a human's neck placed adjacent thereto.

10 Claims, 2 Drawing Sheets

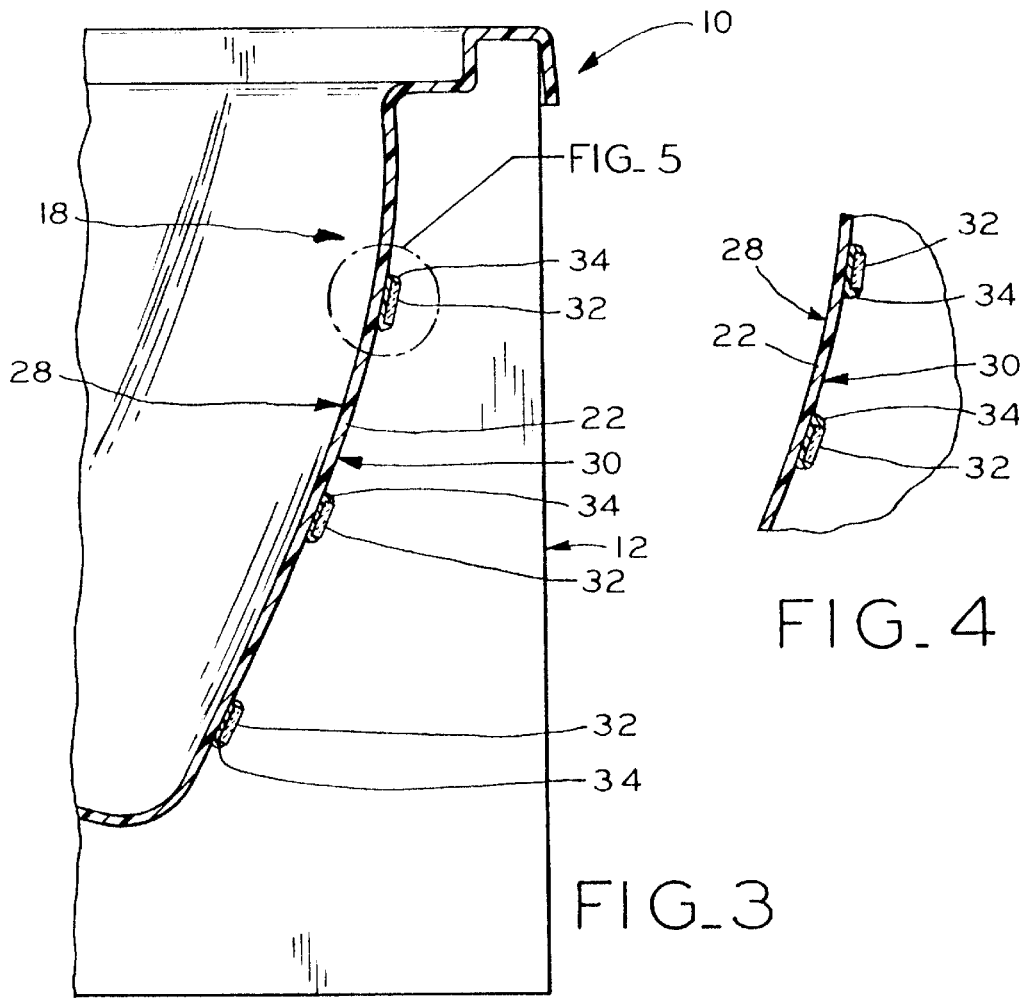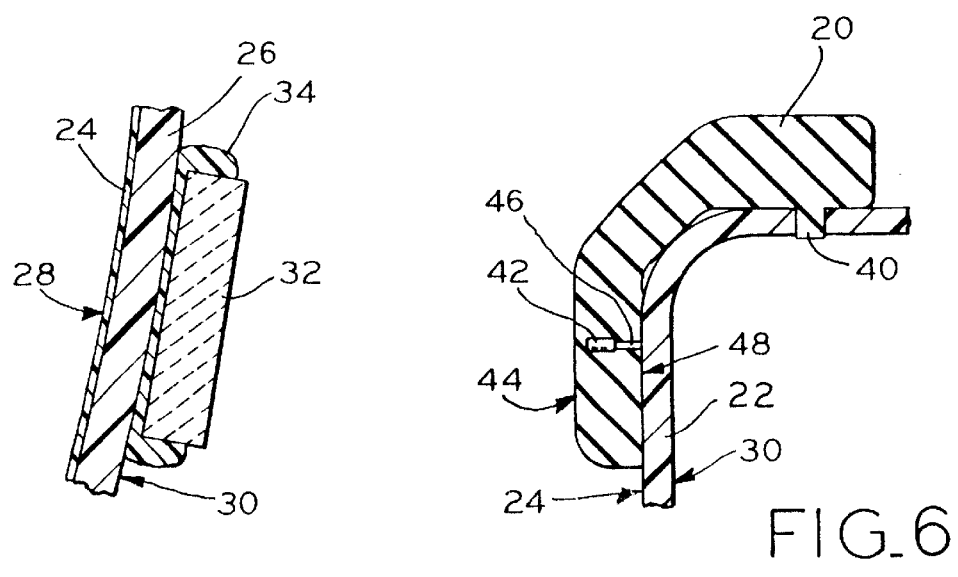

WATER TUB FOR APPLYING MAGNETIC FLUX TO HUMAN BODY

TECHNICAL FIELD

The present invention relates to the field of water tubs also sometimes referred to as bath tubs and spas. More particularly, the present invention relates to a therapeutic water tub for applying magnetic flux to the body of a human using the water tub.

BACKGROUND OF THE INVENTION

Magnetic therapy has been well known as a safe and economic treatment of various aches and pains of the human body. It is believed this is a result of the magnetic properties of hemoglobin. Iron in hemoglobin functions as a carrier of oxygen in addition to playing an important roll in the internal metabolism of cells. Clinical tests have shown that when magnets are applied to painful areas of the body, a favorable reaction takes place. The magnetic flux penetrates the body and creates a magnetic field which is believed to energize and oxygenate the blood, especially the white corpuscles which are the body's natural healing agent. It is believed this creates heat which increases blood flow and which helps the body perform natural healing.

Such therapeutic treatment by applying magnetic flux to the human body is, for example disclosed in Zablotsky et al., U.S. Pat. No. 5,738,624, wherein permanent magnets supported on a face mask are applied to a person's face for therapeutic purposes. Similar applications of magnetic flux have been accomplished by incorporating magnets in shoes and various body bandages and straps. Magnetic therapy has also been used in the treatment of various diseases and arthritis as for example disclosed in Markoll, U.S. Pat. No. 5,842,966; Carlson et al., U.S. Pat. No. 5,693,004; and, Jacobson et al., U.S. Pat. No. 5,366,435.

Although various devices have been devised for magnetic therapy of various parts of the body, and although humans quite often suffer greatly of back and neck pains and aches, there has not yet been devised and a need exists for a device to provide magnetic therapy effectively and efficiently to a human's back and neck so as help alleviate aches and pain through natural healing caused by magnetic therapy.

SUMMARY OF THE INVENTION

It is the principal object of the present invention to provide a means through which magnetic therapy can be applied to a human body, and more particularly a human's back and neck.

In general, the objects of the present invention are accomplished by providing a water tub or spa wherein a human may sit and wherein magnetic flux is applied to the human back and neck. More particularly, a water tub is provided wherein water is retained and having at least one water retaining wall whereagainst a human may rest or otherwise place his back. A plurality of permanent magnets are attached to the outside of the wall with an adhesive. The wall and adhesive are made of substantially non-magnetic materials and the permanent magnets are of sufficient strength such that the magnetic flux field of each magnet travels therethrough and through the inner surface of the water tub whereat the magnetic flux may penetrate the human's back located adjacent the wall inner surface.

A neck support pillow is mounted on the tub wall and is shaped and adapted to receive a neck of a human body adjacent thereto. A plurality of permanent magnets are embedded within the pillow such that the magnetic flux field thereof extends out of the pillow and into the human's neck when placed adjacent thereto.

Preferably, the water tub is a spa type tub having water jets, air jets and heated water. In this manner, a synergistic therapeutic effect is accomplished by both the water therapy and magnetic therapy for helping to relieve aches and pains, alleviate stiffness, reduce swelling and improve circulation.

In one form thereof, the present invention is directed to a water tub for applying magnetic flux to a human body. The tub is adapted to retain water and a human body and includes a wall. A magnet is provided on the wall whereby placement of the human body adjacent the wall and the magnet causes magnetic flux to be applied to the human body. Preferably, the wall forms the tub retaining the water and includes an inside surface facing the water and an outside surface. The magnet is located and affixed on the wall outside surface with an adhesive. The tub wall and adhesive are made of non-magnetic materials for allowing the magnetic flex to travel therethrough and be applied to the human body adjacent the wall inside surface. Preferably, the tub wall includes an acrylic layer and a fiberglass layer sandwiched together.

In one form thereof, the present invention is directed to a water tub for applying magnetic flux to a human body and includes a tub adapted to retain water and a human body. The tub includes a water retaining wall whereon there is provided a neck support pillow. The neck support pillow is adapted to receive a neck of a human body adjacent thereto. A magnet is provided on the neck support pillow whereby magnetic flux is applied to the human neck. Preferably, the neck support pillow is made of compressible foam and one or more magnets are embedded within the compressible foam. Alternatively, one or more cavities extend into the compressible foam and permanent magnets are located within such cavities at depths and locations for placement substantially close to the surface of the neck support pillow whereby the magnetic flux field thereof extends out of the neck support pillow and is applied to a human's neck located adjacent thereto.

BRIEF DESCRIPTION OF THE DRAWINGS

The above-mentioned and other features and objects of this invention and the manner of obtaining them will become more apparent and the invention itself will be better understood by reference to the following description of embodiments of the invention taken in conjunction with the accompanying drawings wherein:

FIG. 3 is a cross sectional view of the tub wall shown in FIG. 2 taken generally along line 3—3;

FIG. 4 is a cross sectional view of the tub wall shown in FIG. 2 taken generally along line 4—4;

FIG. 5 is an enlarged view of a magnet and wall portion shown in FIG. 3; and,

FIG. 6 is a cross sectional view of the neck support pillow shown in FIG. 2 and taken generally along line 6—6.

Corresponding reference characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DETAILED DESCRIPTION OF THE PREFERRED EMBODIMENTS

Figure 1:
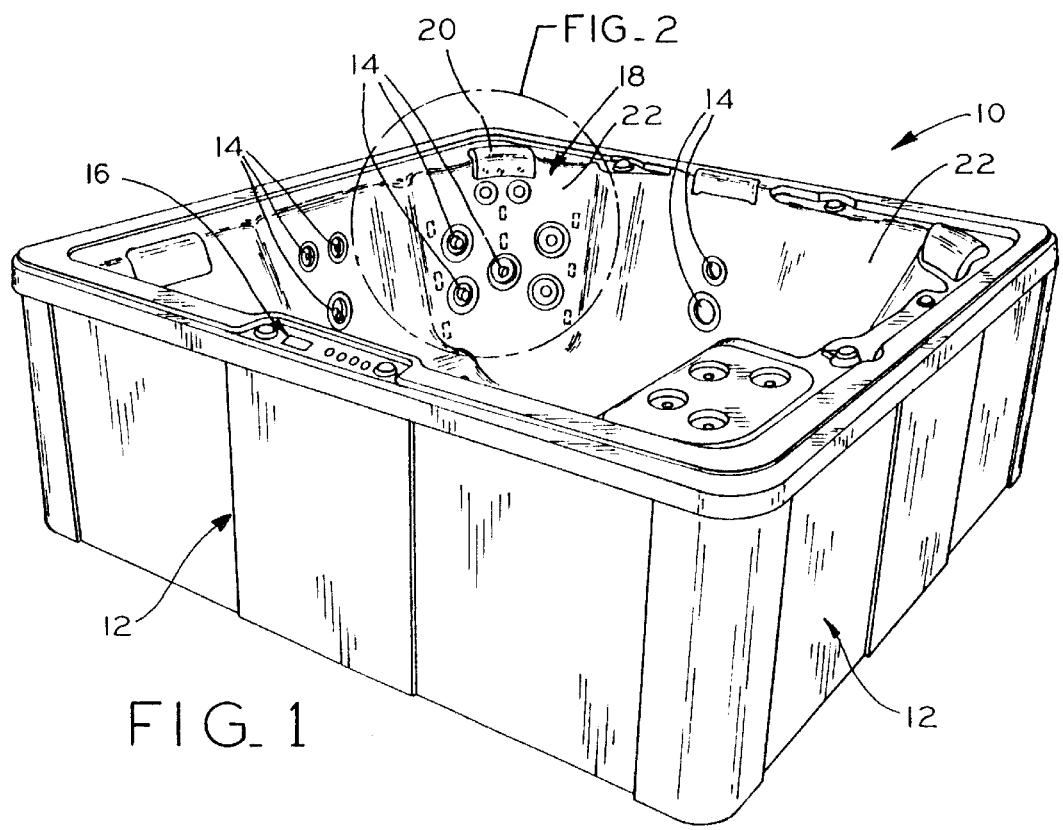
FIG. 1 is a perspective view of a water tub constructed in accordance with the principles of the present invention and incorporating magnets for applying magnetic flux to a human's back and neck.

Referring initially to FIG. 1, a water tub is shown and generally designated by the numeral 10. Water tub 10 is of the spa type and generally includes outer housing or walls 12, water and air jets 14 and controls 16. Water tub 10 operates generally similar to other spas by heating the water therein and circulating the water with or without added air through the jets 14. Water tub 10 includes molded sitting areas throughout the interior thereof and one such sitting area is more particularly shown in FIG. 2 and designated by the numeral 18. As shown, sitting area 18 is molded in a known and customary manner for comfortably retaining a human back thereon. A neck support pillow 20 is mounted and carried generally at the top of the sitting area and similarly is formed for comfortably retaining or supporting a human's neck thereon. It is noted that, as used herein, water tub refers to and is meant to designate all tubs adapted for simultaneously retaining or receiving water and a human body and includes, by way of example, spas and bathtubs.

The water tub 10 is formed and retains water via a wall 22. As shown, preferably wall 22 forms the entire water tub 10 as well as the sitting area 18. As best seen in FIG. 5, most preferably wall 22 is formed and made of an inner acrylic layer 24 and an outer fiberglass layer 26 which are sandwiched and attached together to form a unitary wall 22. Wall 22, thus, includes an inner surface 28 of acrylic and an outer surface 30 of fiberglass. It is noted that acrylic and fiberglass are substantially non-magnetic thereby minimizing the magnetic reluctance and maximizing the magnetic flux extending therethrough as described hereinbelow. Insulation can be wrapped or sprayed onto the fiberglass outer surface 30 if needed, in a known and customary manner (not shown).

A plurality of permanent magnets 32 are provided and are attached to the outer surface 30 of wall 22 with an adhesive 34. Preferably, adhesive 34 is a two-part adhesive comprising a resin and catalyst and having a generally fast curing time and further including a filler material so as to minimize the time necessary for placing and adhering the plurality of magnets 32 as needed throughout the outer surface of wall 22.

Figure 2:
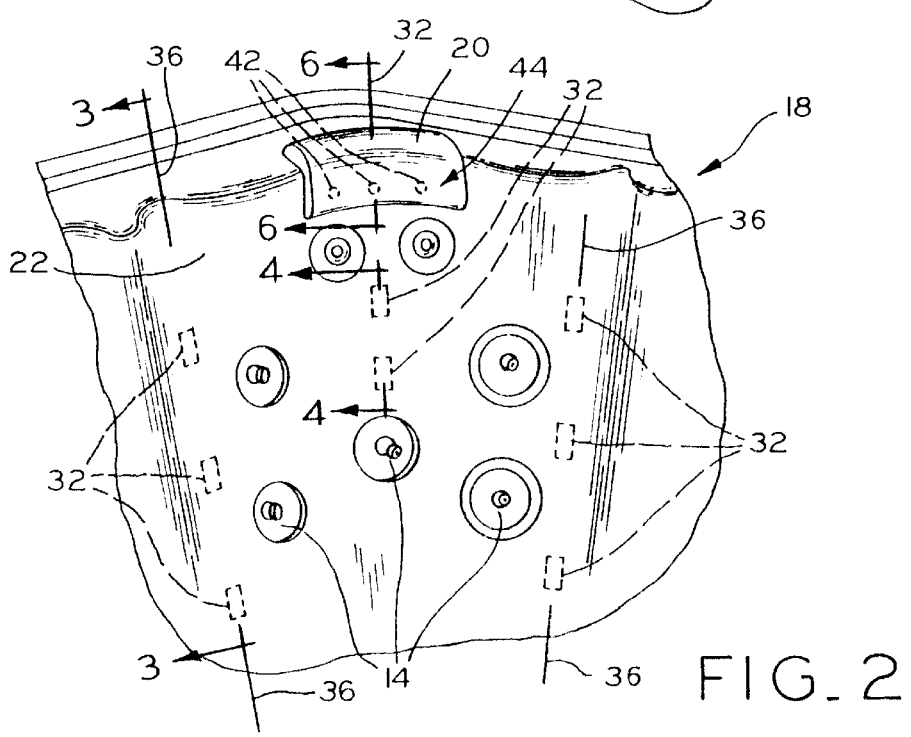
FIG. 2 is an enlarged view of the tub wall and neck support pillow portions of the tub shown in FIG. 1 whereat magnets are provided.

Permanent magnets 32 are preferably made of ceramic materials and have a flux density of at least about 3,000 gauss. In this manner, the magnetic flux field thereof (not shown) will travel through wall 22 and well beyond the inside surface 28, and into the back of a human body sitting adjacent or against the inner surface 28. Magnets 32, as best seen in FIGS. 1 and 2, are also strategically placed and aligned with two outer lines 36 forming a generally V-shape and being located generally closer to the muscle areas of one's back. A line 38 of inner magnets 32 are placed for providing magnetic therapy generally to the middle of one's back as well.

In another embodiment, it is contemplated that permanent magnets 32 can be secured by sandwiching the magnets within the fiberglass layer 26 as the fiberglass layers are applied thereto. In such an embodiment, permanent magnets 32 would be yet more permanently affixed and would be located yet closer to the inner surface 28 thereby maximizing the magnetic flux extending therethrough and into the human's back.

Referring now to FIG. 6, a cross section of the neck support pillow 22 is shown. Neck support pillow 20 is preferably made of compressible water resistant foam. Neck support pillow 20 includes several projections 40 adapted to be received in corresponding holes extending through the tub wall 22. In this manner, neck support pillow 20 is detachably attachable to the upper end of the tub wall 22 as shown.

A plurality of permanent magnets 42 are embedded within pillow 20 generally close to the inside surface 44 thereof. Inside surface 44 is adapted to comfortably receive a human's neck thereon. As best seen in FIG. 2, the inside surface 44 of pillow 20 is generally rounded or circular shaped for providing a snug fit around a human's neck.

Permanent magnets 42 are preferably a rare earth type for minimizing the size thereof and having a flux density of at least about 1,000 gauss. In this manner, the magnetic flux field thereof (not shown) can readily extend out of the pillow and well beyond the inner surface 44 thereof and into a human's neck for thereby providing magnetic therapy. As also shown in FIG. 2, preferably, three magnets 42 are provided and are horizontally aligned with one another thereby applying magnetic flux substantially all around the human's neck when placed thereon.

Magnets 42 are embedded within the neck support pillows 20 by injection molding the magnets 42 directly therein thereby encapsulating the magnets at the correct location. In the alternative, as shown in FIG. 6, a cavity 46 can be formed or drilled into the foam from the back surface 48 thereof. In this embodiment, magnets 42 are located and embedded within a pillow 20 by inserting through the back surface and into the cavity 46 at a desired depth and location with respect to the inner surface 44.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. A water tub for applying magnetic flux to a human body comprising:

a tub adapted to retain water and a human body;

said tub having a wall;

a permanent magnet on said tub wall whereby placement of a human body adjacent said wall causes magnetic flux to be applied to the human body; and, wherein said tub wall retains water and includes an inside surface facing the water and an outside surface, and wherein said magnet is located on said wall outside surface and magnetic flux travels through said wall, whereby magnetic flux is applied to a human body adjacent said wall inside surface.

2. The water tub of claim 1 wherein said magnet is attached to said wall outer surface with an adhesive.

3. The water tub of claim 2 wherein said wall includes an acrylic layer and fiberglass layer sandwiched together.

4. The water tub of claim 2 wherein said wall and said adhesive are made of substantially non-magnetic materials.

5. A water tub for applying magnetic flux to a human body comprising:

a tub adapted to retain water and a human body;

said tub having a wall;

a permanent magnet on said tub wall whereby placement of a human body adjacent said wall causes magnetic flux to be applied to the human body; and, wherein a plurality of magnets are provided on said wall spaced from each other, and wherein said wall is adapted to receive a back of a human body adjacent thereto, whereby magnetic flux is applied to a human back.

6. The water tub of claim 5 wherein said plurality of magnets are attached to said wall with an adhesive.

7. A water tub for applying magnetic flux to a human body comprising:

a tub adapted to retain water and a human body;

said tub having a wall;

a permanent magnet on said tub wall whereby placement of a human body adjacent said wall causes magnetic flux to be applied to the human body; and, wherein said wall is made substantially of non-magnetic materials.

8. The water tub of claim 7 wherein said magnet is attached to said wall with an adhesive.

9. The water tub of claim 7 further comprising a neck support pillow on said tub wall adapted to receive a neck of a human body adjacent thereto, and a magnet on said neck support pillow whereby magnetic flux is applied to a human neck.

10. The water tub of claim 9 wherein said neck support pillow is made of compressible foam and said magnet is embedded within said compressible foam.

* * * * *